(12) United States Patent
Backes

(10) Patent No.: US 11,191,884 B2
(45) Date of Patent: Dec. 7, 2021

(54) SYSTEM FOR DRAINAGE OF FLUIDS OR WOUND SECRETION

(71) Applicant: PFM MEDICAL AG, Cologne (DE)

(72) Inventor: Daniel Backes, Gusenburg (DE)

(73) Assignee: PFM MEDICAL AG, Cologne (DE)

(*) Notice: Subject to any disclaimer, the term of this patent is extended or adjusted under 35 U.S.C. 154(b) by 299 days.

(21) Appl. No.: 15/406,071

(22) Filed: Jan. 13, 2017

(65) Prior Publication Data

US 2017/0203015 A1    Jul. 20, 2017

(30) Foreign Application Priority Data

Jan. 14, 2016 (DE) .................... 20 2016 100 154 U

(51) Int. Cl.
*A61M 35/00* (2006.01)
*A61M 1/00* (2006.01)
*A61M 39/10* (2006.01)
*A61M 39/28* (2006.01)
*A61M 27/00* (2006.01)
*A61M 39/24* (2006.01)
(Continued)

(52) U.S. Cl.
CPC ............ *A61M 1/73* (2021.05); *A61M 1/0001* (2013.01); *A61M 1/0003* (2013.01); *A61M 1/602* (2021.05); *A61M 1/70* (2021.05); *A61M 1/84* (2021.05); *A61M 1/90* (2021.05); *A61M 27/00* (2013.01); *A61M 39/10* (2013.01); *A61M 39/24* (2013.01); *A61M 39/28* (2013.01); *A61M 2205/0216* (2013.01); *A61M 2205/3379* (2013.01); *A61M 2207/00* (2013.01); *A61M 2209/082* (2013.01)

(58) Field of Classification Search
CPC .......... A61M 35/00; A61M 1/00; A61M 3/00; A61M 31/00; A61F 13/00; A61F 13/02; A61F 8/44
See application file for complete search history.

(56) References Cited

U.S. PATENT DOCUMENTS 4,161,179 A * 7/1979 Abramson ........... A61M 1/0011
                                            128/DIG. 24
4,466,888 A * 8/1984 Verkaart ............. A61M 1/0001
                                                 210/232

(Continued)

FOREIGN PATENT DOCUMENTS

CN        204521729 U   *   5/2015
CN        204521729         8/2015
(Continued)

OTHER PUBLICATIONS

Office Action from related Chinese Appln. No. 2017100185957, dated Oct. 28, 2019. English translation attached.

*Primary Examiner* — Tatyana Zalukaeva
*Assistant Examiner* — Ilya Y Treyger
(74) *Attorney, Agent, or Firm* — Grossman, Tucker, Perreault & Pfleger, PLLC

(57) ABSTRACT

The invention relates to a system for drainage of fluids or wound secretion from body and/or tissue openings of the human or animal body comprising a bag-like reservoir for collecting the fluid or wound secretion, with an upper inlet opening and a lower outlet opening, and a pre-evacuated container with an inlet opening, wherein the inlet opening of the pre-evacuated container is connected to the lower outlet opening of the bag-shaped reservoir.

20 Claims, 5 Drawing Sheets

(51) Int. Cl.
    *A61M 3/00*         (2006.01)
    *A61M 31/00*       (2006.01)
    *A61F 13/00*        (2006.01)
    *A61F 13/02*        (2006.01)

(56) References Cited

U.S. PATENT DOCUMENTS

| | | | |
|---|---|---|---|
| 4,525,166 A | 6/1985 | Leclerc | |
| 5,100,376 A * | 3/1992 | Blake, III | A61M 1/02 604/320 |
| 5,683,357 A * | 11/1997 | Magram | A61M 1/0021 604/8 |
| 7,048,724 B2 * | 5/2006 | Grossman | A61M 1/0003 604/319 |
| 8,034,038 B2 * | 10/2011 | Biggie | A61M 1/0096 602/42 |
| 10,441,251 B2 * | 10/2019 | Kerr | A61M 1/0007 |
| 2008/0243089 A1 * | 10/2008 | Keaton | A61M 39/287 604/250 |

FOREIGN PATENT DOCUMENTS

| | | |
|---|---|---|
| DE | 3146266 | 1/1983 |
| DE | 9004314 | 7/1990 |
| WO | 2014/174218 | 10/2014 |
| WO | 2015/086037 | 6/2015 |

\* cited by examiner

SYSTEM FOR DRAINAGE OF FLUIDS OR WOUND SECRETION

FIELD OF THE INVENTION

The invention relates to a system for drainage of fluids or wound secretion from body and/or tissue openings in the human or animal body.

BACKGROUND

Systems for drainage of fluids or wound secretion are known from the prior art. With such system it is possible to free body and/or tissue openings of the human or animal body quickly from accumulated fluids, so that a healing as fast and easy as possible is achieved. An example for an illness, where a system for drainage of fluids or wound secretion is usually used, is the abdominal ascites, in which pathologically serous fluid accumulates in the free cavity of the abdominal cavity.

For drainage of accumulated fluid or wound secretion from the prior art in principal two kinds of drainage are known:

Systems for drainage of the first kind create a suction, so that fluid or wound secretion is suckable. Therefore system exists with a so-called high-vacuum or with a so-called low-vacuum. For creating the suction a vacuum container is used, which is for example evacuated using a pump, so that it contains a vacuum inside. A drainage line is connectable to an opening of the vacuum container, wherein the distal end of the drainage line is connected to body and/or tissue opening of the human or animal body, so that fluid accumulated there is suckable by the created suction. Disadvantageous for these systems is, that the vacuum container has a small capacity, since otherwise the creation of the vacuum for the suction is difficult. Further, the walls of such vacuum containers are rigid, also to allow the creation of the vacuum inside the vacuum container. Thus, such vacuum containers are bulky in storage. Further, such containers are expensive in production and expensive is use, particularly in clinical operation, since a multiple of vacuum containers is used for a drainage due to the limited capacity, which also have to be stored.

Furthermore, from the prior art second kinds of systems for drainage of fluids or wound secretion are known, which function according to the principle of a so-called gravity drainage. For such systems no vacuum is used for the suction of the accumulated fluid or accumulated wound secretion, but only the amount of liquid or wound secretion is passively collected in a container, which is collectable without creation of a suction. The advantage of such systems is that a plastic bag can be used as the collection container for the fluid or wound secretion, which are relatively cheap in production and have a greater capacity compared to vacuum containers. Disadvantageous is the initiation of the drainage is sometimes difficult for such gravity drainage systems.

Starting from this prior art it is an object of the present invention to avoid the disadvantages and provide an improved system for drainage of fluids or wound secretion, which can particularly handle large quantities of fluids or wound secretion and which allow a reliable initiation of the drainage.

SUMMARY

For technically solving this object according to the invention a system for drainage of fluids or wound secretion from body and/or tissue openings of the human or animal body is proposed, which comprises a bag-like reservoir for collecting the fluid or wound secretion, with an upper inlet opening and a lower outlet opening, and a pre-evacuated container with an inlet opening, wherein the inlet opening of the pre-evacuated container is connected to the lower outlet opening of the bag-shaped reservoir.

The invention bases on the findings that the advantages of the systems for drainage of fluids or wound secretion known from the prior art can be combined. Thus, an optimal system for drainage of fluids or wounds secretion allows a secure initiation or initialisation of the drainage and also has a high drainage capacity, so that during use the frequent change of the container for fluid or wound secretion is superfluous.

Therefore the inventive system for drainage of fluids or wound secretion comprises a bag-like reservoir for collecting the fluid or wound secretion and also a pre-evacuated container. The pre-evacuated container is the last element in the system, by connecting an outlet opening of the bag-like reservoir with an inlet opening of the pre-evacuated container. Surprisingly it has emerged that although the pre-evacuated container is the last element in the system the required initial suction for a secure start or initialisation or initiation of the drainage can be provided, even though the suction caused by the vacuum in the pre-evacuated container has to pass the bag-like reservoir during the start of the drainage. Particularly keeping in mind the high capacity of the inventive bag-like reservoir.

After the secure start or secure initialisation of the drainage using the inventive system the pre-evacuated container can be disconnected from the system because the drainage is continued by gravity into the bag-like reservoir.

The inventive system for drainage of fluids or wound secretion is suitable for clinical applications and for home applications.

In an embodiment of the invention the bag-like reservoir is made of a flexible material, preferably of plastic. In such a way multiple bag-like reservoirs can be stockpiled without any problems. Furthermore, such a bag-like reservoir is inexpensive.

A preferred embodiment of the invention provides that the surface of the inner wall of the bag-like reservoir is profiled, so that the drainage is initiated or achieved by the suction of the pre-evacuated container over the bag-like reservoir at the body and/or tissue opening of the human or animal body. Therefore, advantageously rips, nubs, convexities, waves or such the like are formed on the inner wall of the bag-like reservoir. Further, the surface is advantageously ribbed, nubbly, wavy or similar profiled. The convexities can correspond to the surface of a golf ball. The above mentioned profiling of the bag-like reservoir guarantees a secure transfer of the suction caused by the pre-evacuated container over the bag-like reservoir to the body and/or tissue opening of the human or animal body. The profiling of the inner wall of the bag-like reservoir provides air channels, which securely transfer the suction of the vacuum. If the bag-like reservoir consists of several, at least two, elements, advantageously at least one wall, which builds an inner surface of the bag-like reservoir, is profiled as described above.

In a preferred embodiment of the invention the bag-like reservoir has a capacity of about 500 ml to about 5000 ml, particularly preferred the bag-like reservoir has a capacity of about 3000 ml. The capacity of about 3000 ml is an optimal trade-off between a high drainage capacity and the secure initiation or initialisation of the drainage by the suction of the pre-evacuated container.

An embodiment of the invention is characterized in that a tube-like outlet is located at the lower opening of the bag-like reservoir, wherein the lower outlet opening and the tube-like outlet are preferably built integrally or in one par or wherein the lower outlet opening and the tube-like outlet built one unit. The tube-like outlet allows a flexible usage of the inventive system, since the bag-like reservoir and the pre-evacuated container are movable relative each other although they are connected to each other, so that a user can for example fix or hang the bag-like reservoir and the pre-evacuated container at different locations. This is especially advantageous in home applications, since home user do not always have enough space, for example at a stand, to locate the whole system in one place.

In a preferred embodiment the lower outlet opening of the bag-like reservoir is sealable, so that the fluid or wound secretion collected in the bag-like reservoir cannot exit from the lower outlet opening.

Advantageously the lower outlet opening and/or the tube-like outlet of the bag-like reservoir has a clamp device, preferably a so-called slide clamp, which can seal the lower outlet opening. A slide clamp has recess extending in a longitudinal direction, wherein the recess is tapered at one end in such a way, that a tube or such the like, according to the invention the tube-like outlet, arranged inside the recess is clamped. The opposing end of the recess however is wide enough, that the tube located inside the recess is not clamped.

In a further preferred embodiment of the invention the lower outlet opening and/or the tube-like outlet of the bag-like reservoir has a vent, which can seal the lower outlet opening and/or the tube-like outlet. In a preferred embodiment of the invention the vent is a check valve, so that without a manual actuation of a user the check valve only allows a flow of fluid or wound secretion in one direction. Furthermore, the check valve can be integrate into a so-called Luer-Lock connector, so that the Luer-Lock connector can be connected to a corresponding Luer-lock connector which in turn is connected with the inlet opening of the pre-evacuated container.

An embodiment of the invention is characterized in that at the upper inlet opening of the bag-like reservoir a drainage line is located for connecting to the body and/or tissue opening of the human or animal body.

In a preferred embodiment of the invention the bag-like reservoir and the pre-evacuated container are pre-connected. The connection of the bag-like reservoir and the pre-evacuated container happens during the manufacturing of the inventive system, so that user do not have to connect the components themselves. The connection between the bag-like reservoir and the pre-evacuated container is made using a tube. This can have Luer-Lock connectors for easy connection. Further, it is possible to pre-connect a drainage line at the upper inlet opening of the bag-like reservoir during the manufacturing of the system according to the invention. The user of the system according to the invention can directly use such a stock piled system for a necessary drainage.

A further preferred embodiment of the invention provides that the upper inlet opening of the bag-like reservoir has a backflow protection, so that the fluid or wound secretion located in the bag-like reservoir cannot exit from the upper inlet opening of the bag-like reservoir. The backflow protection guarantees that fluid or wound secretion can only flow through the inlet opening of the bag-like reservoir into the bag-like reservoir and not through the inlet opening out of the bag-like reservoir. Particularly during a change of the bag-like reservoir or the disposal of the bag-like reservoir or of the whole system after completion of the drainage a undesired leakage of collected fluid or wound secretion can be prevented. A backflow protection can be designed preferably as a so-called lip-vent, which only allows a flow of fluid or wound secretion or such a like in one direction due to its design and thus provides a backflow protection for the fluid or wound secretion or such the like collected in the bag-like reservoir.

A preferred embodiment of the invention provides that the bag-like reservoir and/or the pre-evacuated container have a holder for hanging and/or mounting preferably at a stand. Furthermore, a scale can be provided at the bag-like reservoir an/or the pre-evacuated container for indicating the amount of fluid or wound secretion inside the bag-like reservoir respectively pre-evacuated container. The scale thus indicates the actual filling capacity.

The invention further comprises the following aspect:

Aspect 1:

Method for drainage of fluids or wound secretion from body and/or tissue openings of a human or animal body, comprising the following steps:

providing an initial suction at a body and/or tissue opening of the human or animal body using a pre-evacuated container, wherein the initial suction of the pre-evacuated container is transferred over a bag-like reservoir arranged between the body and/or tissue opening and the pre-evacuated container, and disconnecting or clamping off the pre-evacuated container from the bag-like reservoir after creation of the initial suction, so that afterwards the fluid or wound secretion is collected inside the bag-like reservoir by a gravity drainage.

Further details, features and advantages of the invention will be described in the following with reference to the embodiments shown in the figures.

DETAILED DESCRIPTION

Figure 1:
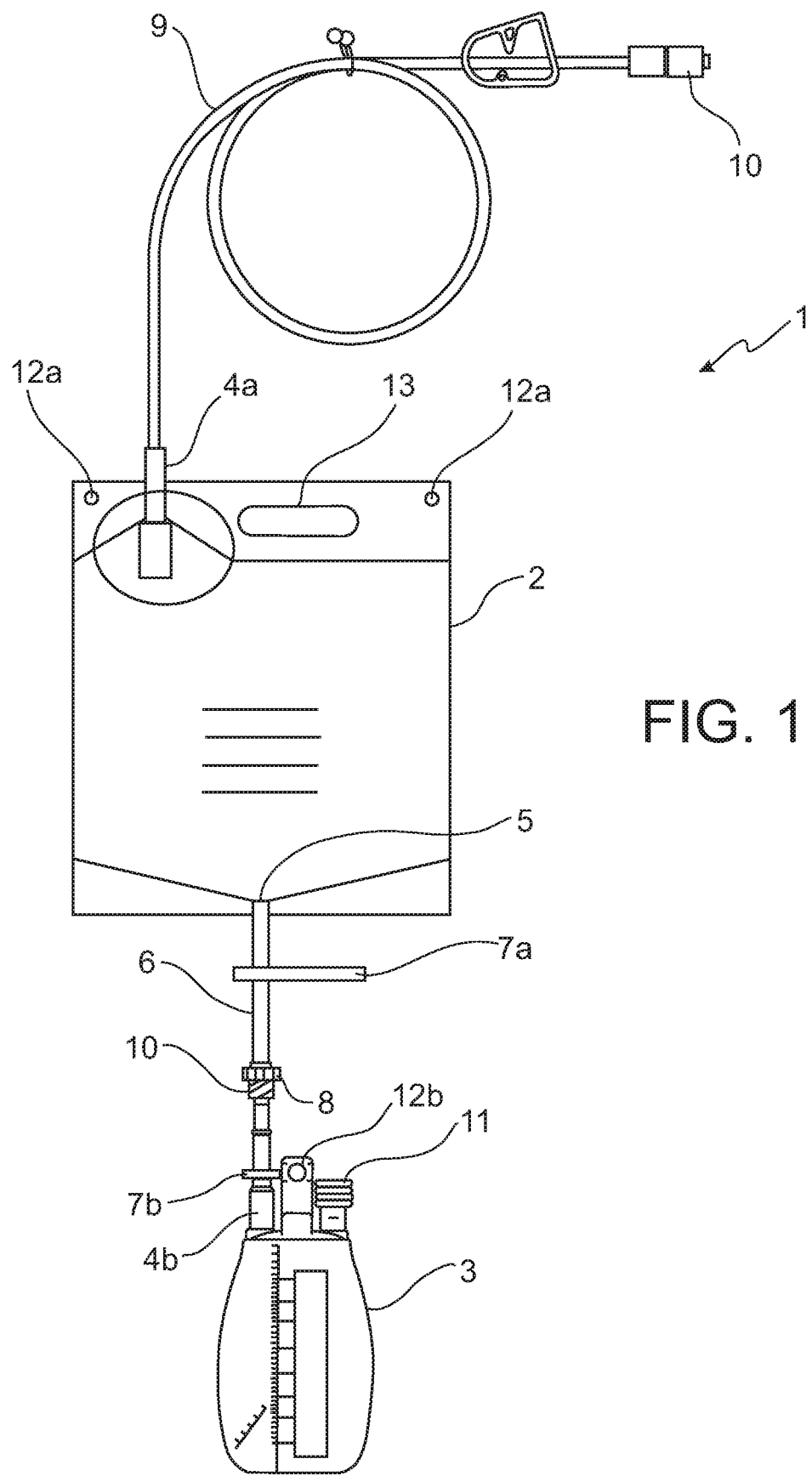
FIG. 1 is a schematic view of an embodiment of a system according to the invention.

In FIG. 1 an embodiment of a system 1 for drainage of fluid or wound secretion from body and/or tissue openings of the human or animal body is shown.

The inventive system 1 comprises a bag-like reservoir 2. The bag-like reservoir 2 has an upper inlet opening 4a and a lower outlet opening 5. Further, the system comprises a container 3. The container 3 is pre-evacuated, thus has a vacuum. Further, the container 3 has an inlet opening 4b, through which fluids or wound secretion can be aspirated into the container 3.

The features "top", "bottom", "upper", "lower" and such the like refer to the use position of the system according to the invention.

The inlet opening 4b of the pre-evacuated container 3 is connected with the outlet opening 5 located at the bottom of the bag-like reservoir 2. The connection between the container 3 and the bag-like reservoir 2 is established using a tube-like outlet 6, wherein the tube-like outlet 6 is directly located at the outlet opening 5 of the bag-like reservoir 2. In a preferred embodiment the lower outlet opening 5 and tube-like outlet 6 of the bag-like reservoir are built integrally or in one-part.

The system further comprises a drainage line 9, wherein the one end of the drainage line 9 is connected to the inlet opening 4a at top of the bag-like reservoir 2. The free end of the drainage line 9 has a Luer-Lock connector 10 with a protection cap, wherein a corresponding Luer-Lock connector can be connected to the Luer-Lock connector 10. For example the Luer-Lock connector 10 of the drainage line 9 of the system 1 according to the invention can be connector an aspirator, so that fluid or wound secretion is transferable from a not shown body or tissue opening of the human or animal body vie the drainage line 9 into the bag-like reservoir 2 and optional additionally through the bag-like reservoir 2 into the pre-evacuated container 3.

Presently the free end of the tube-like outlet 6 of the bag-like reservoir 2 also has a Luer-Lock connector 10, so that the also with a corresponding counter-part provided inlet opening 4b of the pre-evacuated container 3 is connectable to the bag-like reservoir 2.

The container 3 is actually pre-evacuated with about 98000 Pascal [Pa] (corresponding to a high-vacuum drainage) or alternatively with about 40000 Pascal [Pa] (corresponding to a low-vacuum drainage).

With the vacuum inside the pre-evacuated container 3 an initial suction is crated to start the drainage, so that fluids can be transferred from the body and/or tissue opening of the human or animal body into the system 1 according to the invention. The initial suction created by the vacuum guarantees a secure initiation of the drainage. Particularly for gravity drainage which does not use a vacuum to create a suction it is often problematic to initiate the transfer of fluids or wound secretion in a provided reservoir. This disadvantage is avoided by the inventive solution by using the advantage of the initial suction caused by a vacuum to start the drainage.

The inventive solution provokes the suction caused by the pre-evacuated container 3 over the bag-like reservoir 2. Thus, the suction must be strong enough, so that this is possible. Presently at least part of the surface of the inner wall of the bag-like reservoir 2 is profiled. In a preferred embodiment of the invention the inner wall of the bag-like reservoir 2 has rips, nubs or such the like. This allows a better transfer of the suction caused by the pre-evacuated container 3 over the bag-like reservoir 2. The rips, nubs or such the like of the inner walls of the bag-like reservoir 2 built air channels, which help to transfer the suction of the vacuum.

After a successful initialisation of the drainage by the vacuum of the container 3, the pre-evacuated container 3 can be disconnected from the inventive system 1. For comfortably disconnecting the pre-evacuated container 3 from the inventive system 1 a Luer-Lock connection is provided. To avoid that any fluid or wound secretion present at the connection between the outlet opening 5 of the bag-like reservoir 2 and the inlet opening 4b of the container 3 accidentally exits the system 1, a slide-clamp 7b is located above the inlet opening 4b of container 3, which can seal a tube-like clamping part (connection between the inlet opening 4b of the pre-evacuated container 3 and the Luer-Lock connector 10 of the tube-like outlet 6 of the bag-like reservoir 2). Further, the Luer-lock connector 10, which is located at the outlet 6 of the bag-like reservoir 2 and between the bag-like reservoir 2 and the pre-evacuated container 3, has a check valve 8.

Fluid or wound secretion can also be collected in the pre-evacuated container 3, by aspirating the fluid or wound secretion over the bag-like reservoir 2 into the pre-evacuated container 3. For example only after collecting of fluid or wound secretion (as described above) the pre-evacuated container 3 is disconnected from the inventive system 1, so that the fluid or wound secretion collected in the pre-evacuated container 3 can be used for further examinations. The drainage into the bag-like reservoir 2 is unimpaired thereof.

After disconnecting the pre-evacuated container 3 from the inventive system 1 the fluid or wound secretion is solely collected in the bag-like reservoir 2. After disconnecting the pre-evacuated container 3 this functions as a gravity drainage, which is unproblematic since the drainage and thus the liquid flow is already active and sufficiently strong.

The advantage of the inventive system 1 is that the bag-like reservoir 2 provides a high drainage capacity since the capacity of the bag-like reservoir 2 is much bigger than the capacity of the pre-evacuated container 3. Pre-evacuated containers 3 with a high capacity are particularly expensive in manufacturing, whereas bag-like reservoirs 2 with a big capacity are inexpensive in manufacturing. If the pre-evacuated container 3 is only used to start the drainage a further advantage is that the pre-evacuated container 3 can be used multiple times to initiate or initialize the drainage. Due to the bulky contour of the pre-evacuated container 3 these have a high storage requirement. However, this storage requirement can be reduced by reusing the pre-evacuated container 3 as described above. In contrast to this, multiple bag-like reservoirs 2 can be easily stored by the user because of their contour.

In a preferred embodiment the inlet opening 4a of the bag-like reservoir 2 has a backflow protection, so that fluid collected in the bag-like reservoir 2 cannot accidentally exit from the bag-like reservoir 2. Presently the backflow protection is a so-called lip-sealing, which ensures that fluid or wound secretion already collected in the bag-like reservoir 2 cannot exit through the inlet opening 4a of the bag-like reservoir 2, but at the same time ensures further fluid or wound secretion can flow via the lip-vent as backflow protection through the inlet opening 4a into the bag-like reservoir 2.

The outlet opening 5 or the tube-like outlet 6 of the bag-like reservoir 2 is presently provided with a slide-clamp 7a, so that during disconnecting the bag-like reservoir 2 and the pre-evacuated container 3 no fluid collected in the bag-like reservoir 3 can exit.

The pre-evacuated container 3 further has a bellow as a vacuum indicator 11, so that the user can easily identify whether a vacuum is present inside container 3. The bellow as vacuum indicator 11 is fully contracted if a vacuum is inside container 3 and expands stepwise until the container 3 has filled with air and no vacuum is present anymore inside container 3.

The bag-like reservoir 2 as well as the pre-evacuated container 3 can have a scale, so that a user can easily identify the amount of fluid present in the bag-like reservoir 2 or pre-evacuated container 3. Further, the bag-like reservoir 2 as well as the pre-evacuated container 3 can have a mounting or holder 12a or 12b, which can be used to used to fix the bag-like reservoir 2 and/or the pre-evacuated container 3 to a stand, IV-stand or such the like. Furthermore, the bag-like reservoir 2 additionally has a handle 13, presently in form of a handle-hole in the bag-like reservoir 2, so that a user can easily handle the bag-like reservoir 2, for example if the bag-like reservoir 2 has to be replaced after it is full with liquid or wound secretion.

Figure 2A:
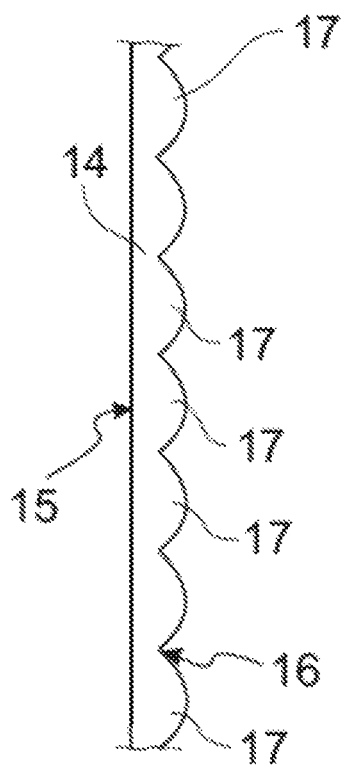
FIG. 2A is a sectional view through the wall of bag-like reservoir according to the invention.
Figure 2B:
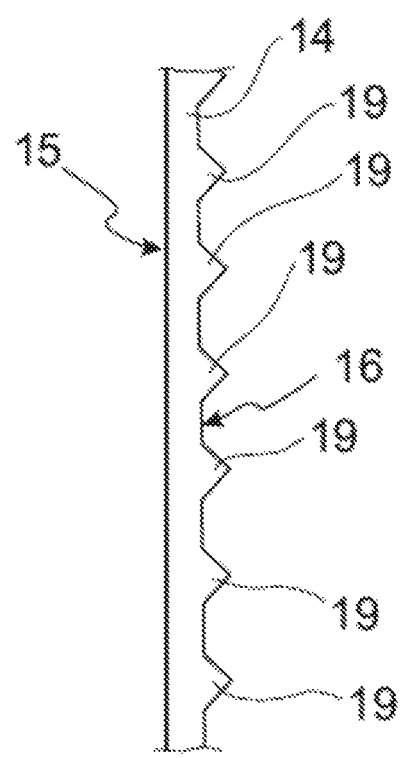
FIG. 2B is another sectional view through the wall of bag-like reservoir according to the invention.

In FIGS. 2a to 2d different embodiments of walls 14 of an inventive bag-like reservoir 2 are shown in sectional views. In FIG. 2a the inner wall 16 of the bag-like reservoir 2 has nubs 17, which are located directly one to another. In contrast to this the inner wall 16 in FIG. 2b has rips 19, which are spaced from one another. Between the rips 19 channels are built for guiding the suction.

Figure 2C:
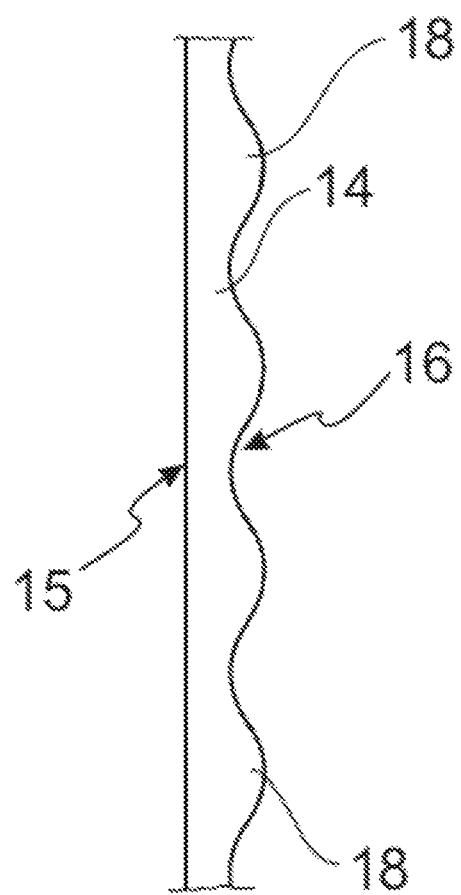
FIG. 2C is another sectional view through the wall of bag-like reservoir according to the invention.
Figure 2D:
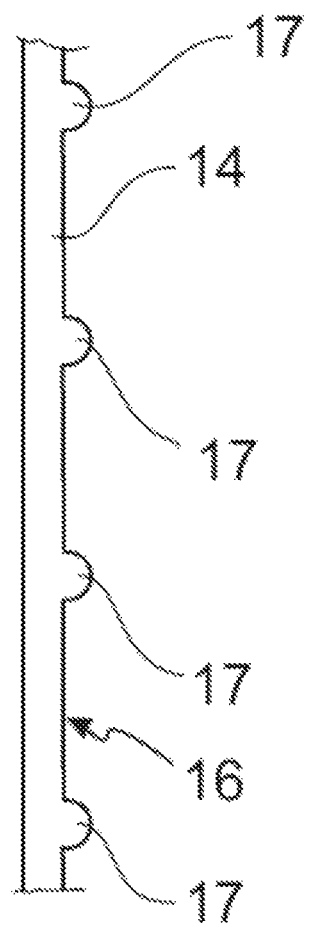
FIG. 2D is another sectional view through the wall of bag-like reservoir according to the invention.

The inner wall according to FIG. 2c is wavy, so that also channels are built between rises or wave elevations 18. In contrast to FIG. 2a the nubs 17 of the inner wall 16 of the bag-like reservoir 2 according to FIG. 2d are spaced from one another.

In all FIGS. 2a to 2d the respective outer wall 15 of the bag-like reservoir 2 is even, wherein the respective outer wall 15 also could be profiled, for example nubbly, ripped, wavy or such the like. Also the inner walls 14 of the bag-like reservoir 2 not shown in FIGS. 2a to 2d opposing the shown walls 14 of the bag-like reservoir 2 could be built correspondingly to the shown walls 14 of the bag-like reservoir 14.

The embodiments shown in the figures and described above are only illustrative and are not limiting the invention.

LIST OF NUMERALS

1 System for drainage of fluids or wound secretion from a body and/or tissue opening of the human or animal body
2 bag-like reservoir
3 pre-evacuated container
4a inlet opening (bag-like reservoir)
4b inlet opening (pre-evacuated container)
5 outlet opening (bag-like reservoir)
6 outlet (bag-like reservoir)
7a slide-clamp (bag-like reservoir)
7b slide-clamp (pre-evacuated container)
8 check valve
9 drainage line
10 Luer-Lock connector
11 vacuum indicator
12a holder/mounting (bag-like reservoir)
12b holder/mounting (pre-evacuated container)
13 handle
14 wall (bag-like reservoir)
15 outer wall (bag-like reservoir)
16 inner wall (bag-like reservoir)
17 nub (inner wall of bag-like reservoir)
18 wave (inner wall of bag-like reservoir)
19 elevation rip (inner wall of bag-like reservoir)

What is claimed is:

1. A system for drainage of fluid secretion from a body and/or a tissue opening of a human or animal body comprising:
   a bag reservoir to collect the fluid secretion, wherein the bag reservoir has an upper inlet opening and a lower outlet opening,
   a pre-evacuated container having an inlet opening, wherein the inlet opening of the pre- evacuated container is connected to the lower outlet opening of the bag reservoir,
   wherein, during an operation of the system, the bag reservoir and the pre-evacuated container are arranged in fluid communication such that drainage is performed in a presence of suction provided by a vacuum of the pre-evacuated container over the bag reservoir,
   wherein the pre-evacuated container is disconnectable from the lower outlet opening of the bag reservoir during the drainage,
   wherein the pre-evacuated container is pre-evacuated prior to being connected to the lower outlet opening of the bag reservoir,
   wherein the lower outlet opening of the bag reservoir is sealable by a sealing device, and
   wherein, when the lower outlet opening of the bag reservoir is sealed by the sealing device, the fluid secretion in the bag reservoir cannot exit from the lower outlet opening.

2. The system according to claim 1, wherein the bag reservoir is made of a flexible material.

3. The system according to claim 2, wherein the bag reservoir is made of plastic.

4. The system according to claim 1, wherein, during the operation of the system, the bag reservoir and pre-evacuated container are arranged in fluid communication such that the drainage is initiatable or achievable by the suction provided by the vacuum of the pre-evacuated container over the bag reservoir.

5. The system according to claim 1, wherein a surface of an inner wall of the bag reservoir is profiled.

6. The system according to claim 1, wherein the bag reservoir has a capacity in a range of about 500 ml to about 5000 ml.

7. The system according to claim 1, wherein a tubular outlet is located at the lower outlet opening of the bag reservoir.

8. The system according to claim 7, wherein the lower outlet opening and the tubular outlet are built integrally.

9. The system according to claim 1, wherein the sealing device is a clamp device.

10. The system according to claim 7, wherein the lower outlet opening and/or the tubular outlet of the bag reservoir are clampable by a clamp device.

11. The system according to claim 10, wherein the clamp device comprises a slide clamp.

12. The system according to claim 7, wherein the lower outlet opening and/or the tubular outlet of the bag reservoir includes a vent to seal the lower outlet opening and/or the tubular outlet.

13. The system according to claim 12, wherein the vent comprises a check valve.

14. The system according to claim 1, wherein a drainage line is located at the upper inlet opening of the bag reservoir for connecting to the body and/or tissue opening of the human or animal body.

15. The system according to claim 1, wherein the bag reservoir and the pre-evacuated container are pre-connected.

16. The system according to claim 1, wherein the upper inlet opening of the bag reservoir has a backflow protection, such that the fluid secretion in the bag reservoir cannot exit from the upper inlet opening of the bag reservoir.

17. The system according to claim 1, wherein the bag reservoir and/or the pre-evacuated container have a holder for hanging and/or mounting.

18. A method for drainage of fluid secretion from a body and/or a tissue opening of a human or animal body, comprising:
   obtaining a system for drainage of the fluid secretion from a body and/or a tissue opening of a human or animal body comprising a bag reservoir to collect the fluid secretion, wherein the bag reservoir has an upper inlet opening and a lower outlet opening, a pre-evacuated container having an inlet opening, wherein the inlet opening of the pre-evacuated container is connected to the lower outlet opening of the bag reservoir, wherein, during an operation of the system, the bag reservoir and the pre-evacuated container are arranged in fluid communication such that drainage is performed in a presence of suction provided by a vacuum of the pre-evacuated container over the bag reservoir, wherein the pre-evacuated container is disconnectable from the lower outlet opening of the bag reservoir during the drainage, wherein the pre-evacuated container is pre-evacuated prior to being connected to the lower outlet opening of the bag reservoir, wherein the lower outlet opening of the bag reservoir is sealable by a sealing device, and wherein, when the lower outlet opening of the bag reservoir is sealed by the sealing device, the fluid secretion in the bag reservoir cannot exit from the lower outlet opening, providing an initial suction at the body and/or the tissue opening of the human or the animal body using the pre-evacuated container, wherein the initial suction of the pre-evacuated container is transferred over the bag reservoir arranged between the body and/or the tissue opening and the pre-evacuated container; and disconnecting or clamping off the pre-evacuated container from the bag reservoir after creation of the initial suction, such that afterwards the fluid secretion is collected inside the bag reservoir by a gravity drainage.

19. The system according to claim 1, wherein the fluid secretion comprises a wound secretion.

20. The system according to claim 1, wherein the pre-evacuated container is connectable to and disconnectable from the lower outlet opening via a connectable/disconnectable connector, and wherein the sealing device is disposed upstream of the connector.

* * * * *